United States Patent
Solfa

(10) Patent No.: US 9,095,638 B2
(45) Date of Patent: Aug. 4, 2015

(54) SYSTEM AND METHOD FOR TEMPERATURE CONTROL IN A TEMPERATURE PROCESSING MACHINE FOR FOOD PRODUCT CONTAINERS

(71) Applicant: SIDEL S.p.A. con Socio Unico, Parma (IT)

(72) Inventor: Andrea Solfa, Parma (IT)

(73) Assignee: SIDEL S.p.A. con Socio Unico (IT)

( * ) Notice: Subject to any disclaimer, the term of this patent is extended or adjusted under 35 U.S.C. 154(b) by 37 days.

(21) Appl. No.: 14/011,279

(22) Filed: Aug. 27, 2013

(65) Prior Publication Data

US 2014/0065014 A1    Mar. 6, 2014

(30) Foreign Application Priority Data

Aug. 30, 2012    (IT) .............................. TO2012A0751

(51) Int. Cl.

| | |
|---|---|
| F26B 3/00 | (2006.01) |
| F26B 7/00 | (2006.01) |
| A01J 11/00 | (2006.01) |
| A23B 4/08 | (2006.01) |
| G05B 1/00 | (2006.01) |
| G05D 23/00 | (2006.01) |
| B65D 85/00 | (2006.01) |
| A61L 2/24 | (2006.01) |
| A23L 3/00 | (2006.01) |
| A23L 3/04 | (2006.01) |

(52) U.S. Cl.
CPC . *A61L 2/24* (2013.01); *A23L 3/003* (2013.01); *A23L 3/04* (2013.01)

(58) Field of Classification Search
CPC .............. A23L 3/00; A61L 2/00; C12H 1/00; C12H 1/08; B65B 55/00; B65B 81/24; H05B 6/00
USPC ............... 422/1, 28, 105, 109, 119, 307–308; 34/343, 380, 391, 337; 99/452, 517; 426/106, 407, 412
See application file for complete search history.

(56) References Cited

U.S. PATENT DOCUMENTS

2009/0117237 A1    5/2009   Hansen et al.
2012/0085071 A1*   4/2012   Hahn et al. ...................... 53/411

FOREIGN PATENT DOCUMENTS

| EP | 1 972 210 A1 * | 9/2008 | ................ A23L 3/00 |
| EP | 1972210 A1 | 9/2008 | |
| WO | WO-00/27227 A1 | 5/2000 | |

OTHER PUBLICATIONS

"Italian Application Serial No. IT T020120751, Search Report dated May 27, 2013", 7 pgs.

Dilay, E., et al., "Modeling, simulation and optimization of a beer pasteurization tunnel", *Journal of Food Engineering,*, 77(3), (2006), 500-513.

* cited by examiner

*Primary Examiner* — Monzer R Chorbaji
(74) *Attorney, Agent, or Firm* — Schwegman Lundberg & Woessner, P.A.

(57) ABSTRACT

A control system for controlling a machine for the temperature processing of containers for food products, having a movement element for moving containers to be processed on a movement path along which at least one temperature-processing zone is defined, the temperature-processing zone being divided into sub-zones each having a respective injection assembly for injecting processing fluid on the containers and a respective adjusting assembly for setting the temperature of the injected processing fluid. The control system is provided with a control unit coupled to the adjusting assemblies of the sub-zones for regulating the temperature of the processing fluid by performing a prediction of the output temperature of the containers located on the movement path based on a current operating condition of the machine and a past thermal trend for the containers, and controlling the adjusting assemblies based on the predicted output temperature.

16 Claims, 3 Drawing Sheets

SYSTEM AND METHOD FOR TEMPERATURE CONTROL IN A TEMPERATURE PROCESSING MACHINE FOR FOOD PRODUCT CONTAINERS

RELATED APPLICATION

This application claims the benefit of priority, under 35 U.S.C. Section 119, to Italian Patent Application Serial No. TO2012A 000751, filed Aug. 30, 2012, which is incorporated herein by reference in its entirety.

BACKGROUND

In some tunnel pasteurisers, food products to be pasteurised, packaged in bottles, cans or other containers, are fed by a conveyor along a forward movement path, which is usually divided into three main processing zones: a heating zone in which the product temperature is gradually raised; a heat-treatment zone in which the product temperature is brought to, and kept at, a pasteurising temperature for a desired time interval; and a cooling zone in which the product temperature is gradually lowered up to a desired output temperature.

At the end of the temperature processing (i.e. at the output of the pasteuriser), it may have been necessary for the food products to have been kept above a predetermined temperature for at least a predetermined time, so as to have accumulated at least a predetermined quantity of pasteurisation units (PUs). In this way, effective pasteurisation of the processed product may be assured.

Each processing zone is, in turn, divided into a plurality of sub-zones, each one of which is operable and controllable independently from the others. The products, in each sub-zone, are processed by injecting thereon a flow of a fluid at a desired predetermined temperature. Usually, the fluid is a liquid, such as water, which is injected, sprayed, or applied in any equivalent manner on the products, although other fluids may as well be used, like a gas, such as air.

For example, each sub-zone comprises a spraying unit positioned above the forward movement path of the products, and, in a possible solution, at least one collection tank positioned below the same forward movement path to collect the liquid, sprayed by the spraying unit, after it has wet the products.

According to some methods, the processing liquid fed to the spraying units of the various sub-zones is taken, at least in part, from the collection tanks.

For example, a process of recirculation is implemented, according to which the liquid fed to the spraying units of the heating sub-zones is taken from the tanks of the cooling sub-zones, whilst the liquid fed to the spraying means of the cooling sub-zones is taken from the tanks of the heating sub-zones. In this way, it is possible to achieve an effective energy saving, thanks to the fact that heat transferred to the processing liquid by the products in the cooling zones may be used to heat the products in the heating zones, while the cooled down processing liquid collected in the heating zones may be used to cool down the products in the cooling zones. Moreover, in the heat treatment zone, the liquid fed to the spraying means of each sub-zone is usually taken directly from the collection tank of that sub-zone.

Suitable temperature-control elements are also envisaged, in order to keep the processing liquid at the desired temperatures in the various zones and sub-zones of the pasteuriser (by warming or cooling the same processing liquid), e.g. including heat exchangers and/or chillers with refrigerating liquid (such as water).

FIG. 1 shows a graph, with time on the x-axis and both temperatures and pasteurisation units on the y-axis, relating to a pasteurisation treatment in the pasteuriser discussed above.

The graph refers to a system operational condition in which each product is fed at a constant speed.

The graph shows: the product theoretical heating thermal trend (dotted curve t); the temperature of the processing liquid injected on the products (continuous curve T); and the accumulation trend of product pasteurisation units (bold continuous curve PU).

Since the speed of the conveyor is assumed constant, the graph may also be interpreted as a portrait of the system condition at each given moment. In this case, the x-axis shows the position of each product along the forward movement path, whilst the y-axis shows the values of the temperature t of the products, the temperature T of the processing liquid and the quantity of pasteurisation units PU accumulated for each product at that specific position.

Accordingly, FIG. 1 also shows the heating zone A, the heat treatment zone B and the cooling zone C. By way of example, each zone is shown as being divided in four subzones, with the direction of the product forward movement being from left to right, as shown by the arrow.

As previously explained, the various temperature-control elements along the path of the products are controllable so that the temperature of the processing liquid in each zone and sub-zone is kept at a desired level, depending on the requirements specific to the products being processed, in order to assure that the products are treated at an appropriate temperature.

For example, in many applications, in order to guarantee the final quality of the processed product, it is required that the output temperature of the products at the end of the treatment is maintained in a desired range, and a control action is required so that the output temperature is not higher than an upper output temperature threshold, nor below a lower output temperature threshold.

In some methods, control of the output temperature is achieved by regulating the temperature of the processing liquid injected on the products in the various sub-zones of the cooling zone of the pasteuriser. For example, for each sub-zone of the cooling zone, the control actions on the temperature-control elements is such that the temperature of the processing fluid is kept below a respective upper limit value.

By way of example, in the pasteurisation of beer products, the upper limit value for the temperature of the processing liquid in the first sub-zone of the cooling zone may be set to 52° C.; while the upper limit value for the temperature of the processing liquid in the last sub-zone of the cooling zone may be set to 29° C., in order to guarantee a desired range for the output temperature of the products, e.g. comprised between 28° C. and 33° C.

The Applicant has realized, however, that the above known control system may have some drawbacks.

For example, it is based on a proper choice for the upper limit values of the temperatures of the processing liquid in the various sub-zones of the cooling zone; these upper limit values are chosen based on empirical data and optimization choices made by expert personnel, and, accordingly, may be biased by errors.

Moreover, problems may arise when the tunnel pasteuriser undergoes unforeseen conveyor stops or when the moving conveyor is not loaded, or it is not fully loaded, with products.

When one of these conditions occur, management of the fluid temperatures in the various processing zones becomes critical, since the thermic regenerative effect between the cooling and heating zones is reduced or absent.

Indeed, when the conveyor is stopped and the product forward movement is interrupted, a general temperature increase occurs in all the zones of the pasteuriser, which may lead to unnecessary injection of refrigerating liquid in the cooling zones (due to the exceeding of the respective upper limit temperatures). Not only this represents a waste of energy, but it may also lead to errors in the output temperature of the products, which may fall outside the desired range (sometimes being lower than the minimum required temperature, other times being higher than the maximum tolerable temperature).

A similar unnecessary power consumption may also occur when the conveyor is not loaded with products, due to the general increase of temperature associated to the reduction of the heat recirculation effect.

SUMMARY

The present disclosure relates to a system and to a method for temperature control in a machine, generally intended for temperature processing of containers designed to contain food products; for example, the following discussion will make reference, without this implying any loss of generality, to control of the cooling temperature in a tunnel pasteurising machine (or pasteuriser) for pasteurising packaged food products.

Embodiments according to this disclosure are configured to solve, at least in part, the problems previously highlighted, including, e.g., to provide a solution for control of the cooling operations, leading to optimization of power consumption and reduction of errors and deviations in the output temperature of the processed products.

In various embodiments, a system and a method for controlling temperature in a machine for temperature processing of containers for food products are provided, as defined in the annexed claims.

BRIEF DESCRIPTION OF THE DRAWINGS

For a better understanding of the present invention, embodiments thereof are now described, purely by way of non-limiting example, with reference to the attached drawings, wherein.

DETAILED DESCRIPTION

Figure 1:
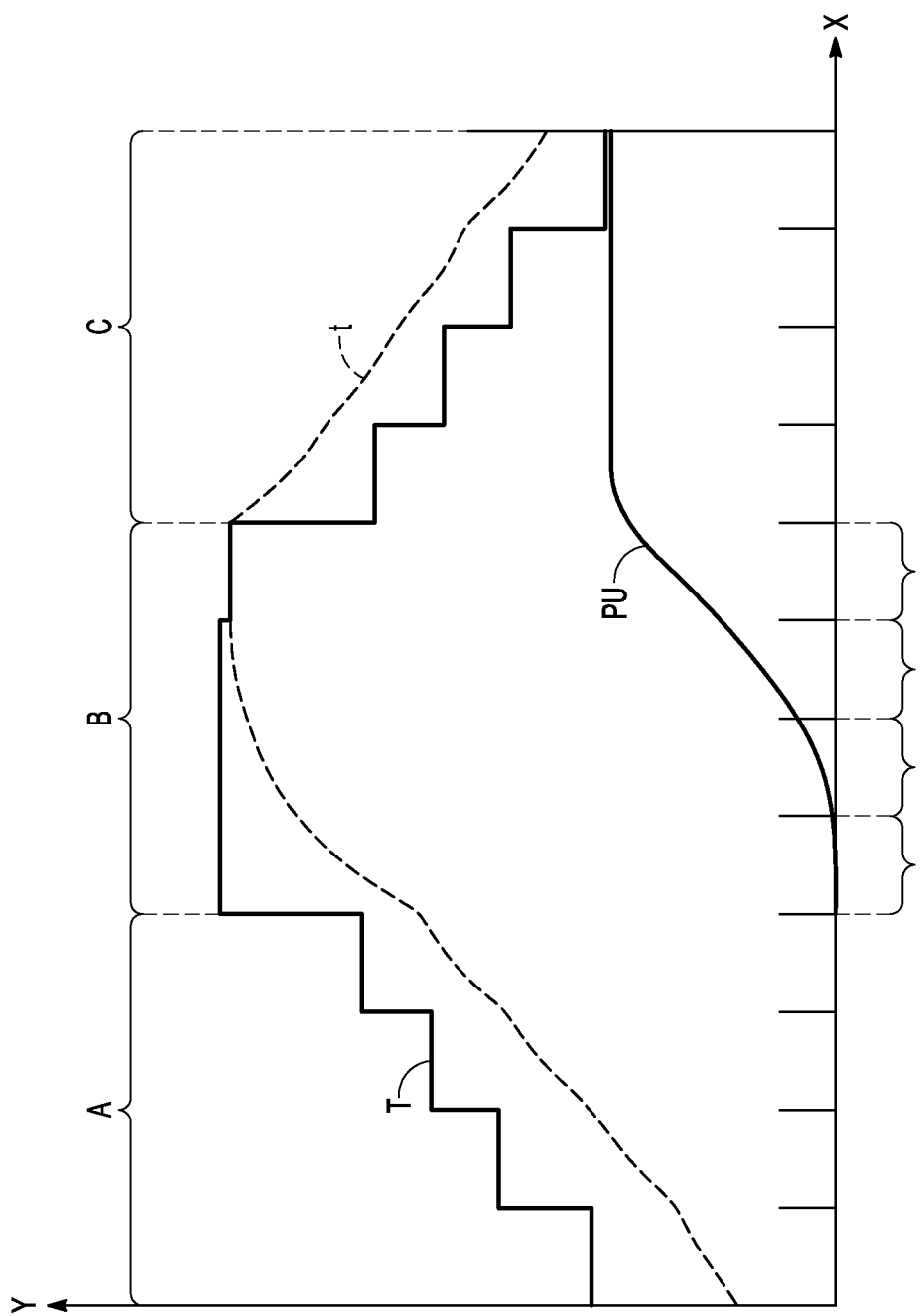
FIG. 1 shows a plot of quantities related to a pasteurising process.
Figure 2:
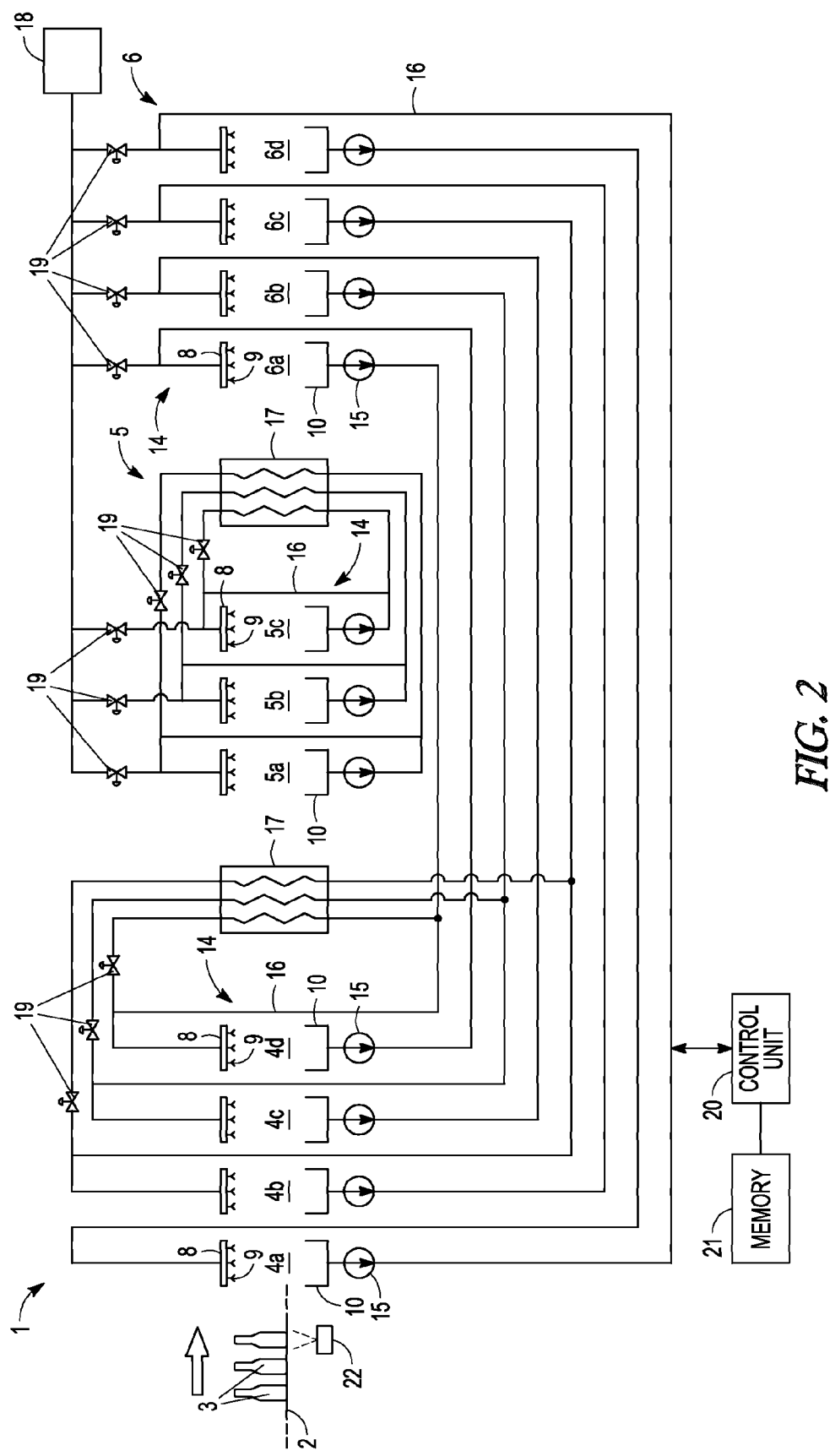
FIG. 2 shows a schematic representation of the layout of a pasteurising machine, where a control system according to this disclosure may be implemented.

FIG. 2 schematically shows a tunnel pasteurising machine, denoted as a whole with 1, including a forward movement element 2, which may consist, for example, of one or more conveyor belts or any other type of conveyor, for moving containers 3 containing products to be pasteurised (e.g. bottles, as shown in the drawing) along a forward movement path.

The machine 1 includes a heating zone 4, a heat treatment zone 5 and a cooling zone 6 positioned one after another along the forward movement path, in order to carry out pasteurisation of the products in the containers 3.

Each one of the heating, heat treatment and cooling zones 4, 5, 6 is further divided into a number of sub-zones positioned one after another along the same forward movement path; in the exemplary embodiment shown in FIG. 2, the heating zone 4 is divided into four sub-zones 4a-4d; the heat treatment zone 5 is divided into three respective sub-zones 5a-5c; and the cooling zone 6 is divided into four respective sub-zones 6a-6d.

Each one of the above sub-zones is provided with a respective spraying or injecting element 8 for spraying or injecting a processing fluid 9 (for example water) onto the containers 3 that are carried by the forward movement element 2 in the same sub-zone, and with a respective collecting element 10, e.g. a tank, for collecting the processing fluid 9 after it has been sprayed on the containers 3 (i.e. after it has exchanged heat with the same containers 3). In the shown embodiment, the spraying element 8 and the collecting element 10 are positioned above and, respectively, below the forward movement path defined by the forward movement element 2, so as to exploit the gravity effect for the movement of the fluid.

In a known manner, which is not shown in detail, a fluid system 14 is associated to each spraying element 8, for controlling spraying of the processing fluid 9 and feeding thereof.

The fluid system 14 includes a pump 15, e.g. a centrifugal pump, coupled to a respective collecting element 10, a fluid duct 16 feeding the spraying element 8, and regulating elements controllable to regulate the temperature of the processing fluid 9 to be sprayed.

The regulating elements may include: heat exchangers and/or chillers 17, which may be e.g. coils immersed in the water of the collecting elements 10, or a tube nest, installed outside the collecting elements 10 and in line with the delivery port of each pump 15; an external cold source 18, which may provide a refrigerating liquid; and suitable valves 19 coupled to the respective fluid duct 16.

Again in a known manner, the fluid systems 14 are controlled to implement recirculation of the processing fluid 9, so that the processing fluid 9 fed to the spraying elements 8 of the heating sub-zones 4a-4d is taken from the collecting elements 10 of the cooling sub-zones 6a-6d, and the processing fluid 9 fed to the spraying elements 8 of the cooling sub-zones 6a-6d is taken from the collecting elements 10 of the heating sub-zones 4a-4d, in order to achieve a energy saving.

Additional temperature regulation, in addition to the one directly provided by the recirculation process, is achieved by suitable control of the regulating elements.

In a way that is not shown, filter elements may be coupled to the collecting elements 10, for preventing contaminants from infiltrating the processing fluid 9.

Moreover, movable elements may be provided to direct the collected fluid from one collecting element 10 towards another one, in order to provide further means for recirculation of the processing fluid 9, as disclosed e.g. in EP-A1-2 058 386, which is incorporated herein by reference in its entirety.

The pasteurising machine 1 further comprises a control unit 20, including a microprocessor or other suitable processing element, coupled to the fluid systems 14 of the spraying elements 8, in order to control the pasteurisation process, including, e.g., the temperature of the processing fluid 9 sprayed by each one of the spraying elements 8. The control unit 20 may be included in an industrial PC designed to control the general operation of the pasteurising machine 1.

The control unit 20 is provided with a memory 21, where instructions, configuration information and data are stored, and receives feedback signals from sensors coupled to the spraying elements 8, including temperature sensors (not shown) for detecting the temperature of the processing fluid 9 sprayed by the same spraying elements 8.

According to an aspect of the present disclosure, the control unit 20 is also coupled to a presence (or proximity) sensor 22, arranged at the entrance of the pasteurising machine 1, at the start of the forward movement path defined by the forward movement element 2. The presence sensor 22, e.g. including a capacitive sensor, an inductive sensor, an IR sensor, an electromagnetic sensor, or any suitable known sensor element, is configured to detect the presence of containers 3 entering the pasteurising machine 1. Product-presence information detected by the presence sensor 22 are conveyed to the control unit 20, which, thanks to the further knowledge of the moving speed (usually constant) of the forward movement element 2, is able to keep track of the presence of the containers 3 along the whole forward movement path.

The control unit 20, at each time of the operation of the pasteurising machine 1, is thus able to know the position of the various containers 3 inside the pasteurising machine 1, including with respect to the spraying elements 8 of the various sub-zones of the heating, heat treatment and cooling zones 4, 5, 6; in other words, the presence information provided by the presence sensor 22 are tracked along the whole forward movement path and the whole processing cycle experienced by the containers 3 inside the pasteurising machine 1.

According to an aspect of the present disclosure, the control unit 20 is designed to control cooling of the containers 3 within the cooling zone 6 of the pasteurisation process, based on the monitoring of the temperature of the same containers 3, including based on a predicted output temperature, which the products will reach at the end of the pasteurisation treatment. In other words, differently from known methods, the present solution envisages direct monitoring of a parameter (temperature) of the products or containers 3, instead of parameters of the pasteurising machine 1 (such as the temperature of the processing fluid 9 injected by the spraying elements 8).

The cooling process is controlled by adjusting the temperature of the spraying elements 8 arranged in the sub-zones 6a-6d of the cooling zone 6, by means of the regulating elements of the respective fluid systems 14.

Figure 3:
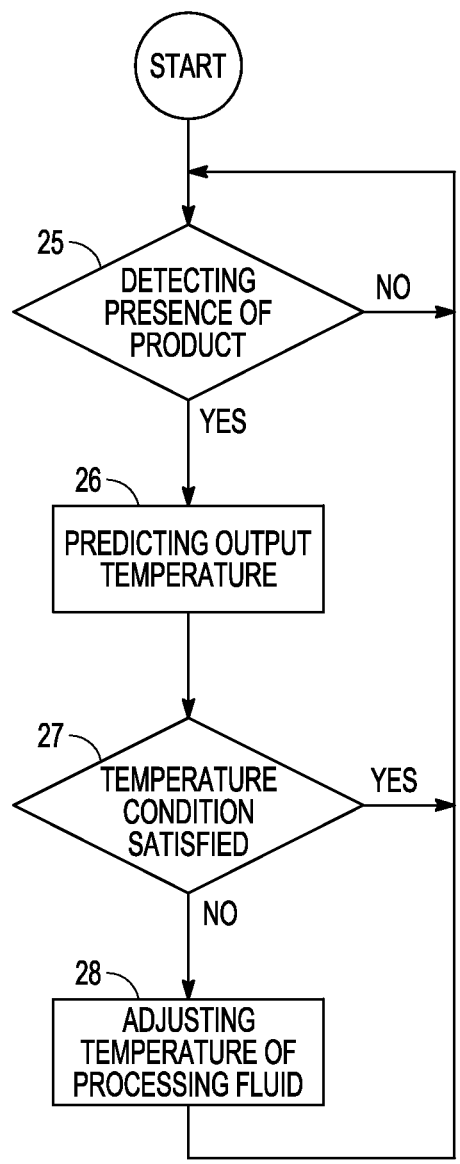
FIG. 3 is a flow chart relating to operations performed by the control system, according to an aspect of this disclosure.

For example, as shown in FIG. 3, the control unit 20 performs the following operations in a cyclical manner (e.g. every two seconds):

detecting, step 25, the presence of containers 3 at selected locations along the forward movement path, based on the presence information detected by the presence sensor 22 and the tracking of the same presence information (for example, the selected locations may be arranged each one in a respective sub-zone 6a-6d of the cooling zone 6);

for each located container 3, step 26, predicting the output temperature that the same container will have at the output of the pasteurising machine 1, at the end of the forward movement path defined by the forward movement element 2, i.e. after the pasteurisation treatment is completed (accordingly, in some cases, the prediction step is carried out only if, and where, the products are effectively present inside the pasteurising machine 1); and in case the predicted output temperature for the located container 3 does not satisfy a desired condition (e.g. it is below a lower limit value or above a higher limit value), as checked at step 27, adjusting, step 28, the temperature of the processing fluid 9 sprayed by one or more of the spraying element 8 at, and/or downstream, the location of the located container 3 with respect to the forward movement path.

For example, the control unit 20 may suitably adjust the temperature for the sole spraying element 8 in the sub-zone 6a-6d of the cooling zone 6 where the container 3 has been located, or adjust the temperature of some or all of the spraying elements 8 arranged downstream the location of the container 3.

No adjusting operation is instead performed in case the output temperature for the located product 3 satisfies the desired condition (e.g. it is comprised between the lower and higher limit values).

The control unit 20 is able to predict the output temperature of the located containers 3 based on the monitoring of the thermal trend followed by the products during the upstream portion of the forward movement path with respect to their detected location, and the current operating condition of the pasteurising machine 1, including the temperature currently set for the processing fluid 9 at the spraying elements 8 in the same detected location and downstream thereof.

For example, a temperature predicting method as disclosed in EP-A1-1 972 210 may be implemented by the control unit 20; in this respect, it is noted that EP-A1-1 972 210 discloses a temperature prediction algorithm for predicting the correct outcome of the pasteurisation treatment in the heat treatment zone 5, and in particular to avoid an excessive pasteurisation, or, on the contrary, to avoid that the products receive an insufficient number of PUs. EP-A1-1 972 210 is incorporated herein by reference in its entirety. Temperature prediction within the heat treatment zone 5 is aimed at achieving a correct number of PUs for the products to be pasteurized; temperature prediction is neither disclosed, nor hinted to for other control purposes.

The temperature predicting method envisages monitoring of the containers 3 at a plurality of reference points distributed one after another along the forward movement path, in order to follow the thermal treatment of the products in the pasteurising machine 1; advantageously, the reference points may be evenly distributed along the whole path.

For example, a number of data are detected and stored by the control unit 20 for the containers 3 located at each reference point, among which: the current temperature of the containers 3 (that is estimated based on the previous thermal trend and the thermal coefficient exchange with the processing fluid 9 at the current location); the temperature of the processing fluid 9 injected at the current location; the time elapsed since entering the pasteurisation tunnel; any dwell time at the current location; the feeding speed of the forward movement element 2; the pasteurisation units accumulated up to the current moment (calculated based on the product thermal trend).

Experimental data and empirical formulas are used to calculate the temperature of the products and the accumulated pasteurisation units. For example, in the case of pasteurisation of beer, the quantity of pasteurisation units accumulated (APU) after the product has remained at a temperature t (expressed in degrees Centigrade) for one minute may be calculated as follows:

$$\Delta PU = 10^{\frac{t-60}{7}}$$

The output product temperature may then be predicted, based on the data stored for the same products up to the current moment and at least one predicted system future operating condition. For example, if the condition of the containers 3 at each reference point is known, then, supposing movement at constant speed from that moment onwards and a predetermined fluid temperature in the actual zone and in each successive zone and sub-zone, it is possible to calculate the thermal trend to which the individual containers 3 will be subjected in the remaining portion of the forward movement path, up to the output of the pasteurising machine 1, and therefore estimate their output temperature.

The prediction of the output temperature is then continuously and cyclically updated based on the situation of the pasteurising machine 1, and any change occurred, e.g. any modification of the temperature of the processing fluid 9 required to satisfy the output temperature specifications.

The advantages of the present solution are evident from the foregoing description.

In any case, it is again emphasized that it allows a considerable saving in the consumption of energy required for the temperature processing of the containers; for example, in a pasteurising machine, it allows saving of energy required for cooling and a corresponding saving of refrigerating liquid.

Moreover, it allows to achieve a higher reliability in the control of the temperature of the products, thanks to the direct monitoring of the output temperature of the containers 3.

These advantages are particularly relevant when the pasteurising machine is not loaded or not fully loaded.

The discussed solution may also be easily fitted (so called "retro-fit" operation) to existing machines, by suitable reprogramming of the related control unit, so as to implement the discussed algorithm based on the presence of products and their predicted output temperature.

Finally, modifications and variations may be made to what has been described and illustrated herein, without thereby departing from the scope of the present invention, as defined in the annexed claims.

For example, other types of machines may be equally controlled, wherever control of an output temperature of processed products is to be achieved, so that it is maintained in a desired range of values.

For example, the discussed solution may be implemented in a bottle washer, to control the output temperature of the cleaned bottles; in a warmer or a cooling machine, to control the heating or cooling temperature of treated bottles or other containers.

Moreover, in addition to the control algorithm discussed, a concurrent temperature control on the temperature of the spraying elements 8 of one or more sub-zones may be implemented.

For example, a concurrent control of the temperature of the processing fluid 9 at output from the spraying elements 8 of the last sub-zone 6d of the cooling zone 6 and/or of the first sub-zone 6a of the same cooling zone 6 may be implemented by the control unit 20, in order to avoid thermal shocks to the products 3 and/or over-pasteurisation thereof.

The invention claimed is:

1. A control system for controlling a machine for the temperature processing of containers for food products, the machine including a movement element for moving the containers to be processed on a movement path along which at least one temperature-processing zone is defined, where the temperature of the containers is to be brought to a desired value, the temperature-processing zone being divided into a number of sub-zones each having a respective injection assembly for injecting processing fluid on the containers and a respective adjusting assembly for setting the temperature of the injected processing fluid; a presence sensor located at the input of said movement path and configured to detect the presence of containers at input to said machine; the control system, comprising:

a control unit operatively coupled to the adjusting assemblies of the sub-zones in order to regulate the temperature of the processing fluid, wherein the control unit is operatively coupled to the presence sensor and is configured to: locate the position of containers along said movement path based on presence information provided by said presence sensor;

wherein said control unit is configured to: perform a prediction of an output temperature of the containers located on said movement path based on a current operating condition of the machine, a past thermal trend for said containers and the located position of the containers along said movement path; and control said adjusting assemblies based on the predicted output temperature, wherein the output temperature of the containers located on said movement path comprises a temperature the containers would reach at output from said temperature-processing zone.

2. The control system according to claim 1, wherein the temperature-processing zone is a cooling zone, where temperature of the containers is to be lowered up to a desired value.

3. The control system according to claim 1, wherein the control unit is configured to control the adjusting assemblies of the sub-zones arranged in correspondence of, or downstream with respect to, the located container along said movement path.

4. The control system according to claim 1, wherein the control unit is configured to compare the predicted output temperature with a lower limit value and/or a higher limit value, and to control said adjusting assemblies based on the result of the comparison.

5. The control system according to claim 4, wherein the control unit is configured to control the adjusting assemblies in order to modify the temperature of the processing fluid, in case the predicted output temperature is below said lower limit value and/or above said higher limit value.

6. The control system according to claim 1, wherein the control unit is configured to identify, at least for a sub-zone of the temperature-processing zone, a number of reference points distributed one after another along the movement path; and, cyclically: for the containers located at each reference point, store data relating to the temperature processing to which they have been subjected up to that point, in order to define the past thermal trend of said products.

7. The control system according to claim 6, the machine being a pasteuriser, and the movement path further defining at least one heating zone, where temperature of the containers entering the machine is raised, and a heat treatment zone, consecutive to the heating zone along the movement path, where the products are designed to receive a desired pasteurisation treatment; each one of the heating and heat-treatment zones being divided into a plurality of sub-zones (each sub-zone having a respective injection assembly for injecting processing fluid on the containers and a respective adjusting assembly for regulating the temperature of the processing fluid; wherein the control unit is configured to additionally identify a number of said reference points at least for a sub-zone of the heating zone and/or for a sub-zone of the heat treatment zone.

8. The control system according to claim 7, wherein the temperature-processing zone is a cooling zone, consecutive to the heat treatment zone along the movement path, where temperature of the containers is to be lowered up to a desired value; the machine further including, for each sub-zone of said heating zone, heat-treating zone and cooling zone, a respective collecting assembly for collecting the processing fluid injected on the containers; the collecting assembly of at least one sub-zone of said cooling zone being fluidically coupled to the injection assembly of a corresponding sub-zone of said heating zone, and the collecting assembly of at least one sub-zone of said heating zone being fluidically coupled to the injection assembly of a corresponding sub-zone of said cooling zone.

9. The control system according to claim 1, further comprising temperature sensors, designed to detect the temperature of the processing fluid at least at said subzones of said temperature-processing zone, in order to define the current operating condition of the machine.

10. A machine for the temperature processing of containers for food products, including a movement element for moving containers to be processed on a movement path along which at least one temperature-processing zone is defined, where the temperature of the containers is brought to a desired value, the temperature-processing zone being divided into a number of sub-zones each having a respective injection assembly for injecting processing fluid on the containers and a respective adjusting assembly for setting the temperature of the processing fluid,
wherein the machine comprises a control system according to claim 1.

11. A control method for controlling a machine for the temperature processing of containers for food products, the machine including a movement element for moving containers to be processed on a movement path along which at least one temperature-processing zone is defined, where the temperature of the containers is brought to a desired value, the temperature-processing zone being divided into a number of sub-zones each having a respective injection assembly for injecting processing fluid on the containers and a respective adjusting assembly for setting the temperature of the processing fluid; the control method, comprising:
sensing the presence of containers at the input of said movement path;
regulating the temperature of the processing fluid, wherein the step of regulating comprises:
locating the presence of the containers along said movement path based on said step of sensing;
performing a prediction of an output temperature of the containers located on said movement path based on a current operating condition of the machine, a past thermal trend of said products and the located position of the containers along said movement path; and
controlling said adjusting assemblies based on the predicted output temperature, wherein the output temperature of the containers located on said movement path comprises a temperature the containers would reach at output from said temperature-processing zone.

12. The control method according to claim 11, wherein the step of regulating includes comparing the predicted output temperature with a lower limit value and/or a higher limit value, so as to control said adjusting assembly based on the result of the comparison.

13. The control method according to claim 12, wherein the step of regulating includes controlling the adjusting assembly in order to modify the temperature of the processing fluid, in case the predicted output temperature is below said lower limit value and/or above said higher limit value.

14. The control method according to claim 11, wherein the step of regulating includes controlling the adjusting assemblies of the sub-zones located at, or downstream with respect to, the located container along said movement path.

15. The control method according to claim 11, wherein the step of regulating includes identifying, at least for a sub-zone of the temperature-processing zone, a number of reference points distributed one after another along the movement path; and, cyclically: for the containers located at each reference point, storing data relating to the temperature processing to which they have been subjected up to that point, in order to define the past thermal trend of said products.

16. The control method according to claim 15, the machine being a pasteuriser, and the movement path further defining at least one heating zone, where temperature of the containers entering the machine is raised, and a heat treatment zone, consecutive to the heating zone along the movement path, where the containers are designed to receive a desired pasteurisation treatment, wherein the temperature-processing zone is a cooling zone, consecutive to the heat treatment zone along the movement path, where temperature of the containers is to be lowered up to a desired value; each one of the heating and heat-treatment zones being divided into a plurality of sub-zones, each sub-zone having a respective injection assembly for injecting processing fluid on the containers and a respective adjusting assembly for regulating the temperature of the processing fluid; wherein the step of identifying includes additional identification of a number of said reference points at least for a sub-zone of the heating zone and/or for a sub-zone of the heat treatment zone.

* * * * *